United States Patent [19]

Smith

[11] 4,171,354

[45] Oct. 16, 1979

[54] VACCINE FOR ANIMAL RESPIRATORY DISEASES

[75] Inventor: Clyde K. Smith, Wooster, Ohio

[73] Assignee: Ohio Agricultural Research and Development Center, Wooster, Ohio

[21] Appl. No.: 809,292

[22] Filed: Jun. 23, 1977

[51] Int. Cl.² ............................................ A61K 39/02
[52] U.S. Cl. ...................................................... 424/92
[58] Field of Search ......................................... 424/92

[56] References Cited

U.S. PATENT DOCUMENTS 3,855,408  12/1974  Maheswaran ........................... 424/92

OTHER PUBLICATIONS

Difco Laboratories Catalog, Nov. 1968, pp. 370, 54, 474–475, 109, Detroit, Michigan.
Gale et al., "Studies on Shipping Fever of Cattle, I, Experimental Exposure of Cattle with Various Cultures of Pasteurella", American Journal of Veterinary Research 19, (1958), pp. 815–817.

Merck Veterinary Manual, Fourth Edition, 1973, pp. 1407–1410.
Remington's Practice of Pharmacy, Tenth Edition, Mack Publishing Co., pp. 1209–1212.
Baldwin et al., "Experimental Infection of Calves with Myxovirus Parainfluenza 3 and Pasteurella Hemolytica", American Journal of Veterinary Research, 28, (1967), pp. 1773–1782.

*Primary Examiner*—Donald G. Daus
*Assistant Examiner*—M. C. Eakin
*Attorney, Agent, or Firm*—Millard, Cox & Smith

[57] ABSTRACT

An improved vaccine and method for immunizing cattle to Shipping Fever Complex type Bovine Respiratory Disease (BRD) which employs an intradermally administered vaccine containing a live culture of Pasteurella sp., particularly, *Pasteurella hemolytica*. Innoculation is carried out before the animals are subjected to stress factors, including weaning and transportation to feedlots. Also described is a method for preparing the vaccine by incubation of *P. hemolytica* within an infusion broth.

10 Claims, No Drawings

VACCINE FOR ANIMAL RESPIRATORY DISEASES

BACKGROUND

Bovine respiratory disease (BRD) currently accounts for annual losses to the beef cattle industry of about 225 millions of dollars. Considered by major feeder cattle associations and livestock groups as the principal disease problem encountered with beef cattle, the malady represents an estimated death loss amounting to an annual 220 million pounds of carcass beef. The most prevalent of the respiratory diseases is generally known as "Shipping Fever Complex" and is a member of the triumvirate of bovine respiratory diseases (BRD) of feedlot cattle along with Viral Bovine Rhinotracheitis (VBR) and Calf Diptheria. BRD (Shipping Fever Complex) is found to occur in cattle of both sexes, six to twenty-four months of age. The incidence, greatest during late autumn and winter, develops within about ten days of arrival of cattle in feedlots.

While the pathogenesis of shipping fever complex has not been fully elucidated, investigators have deduced three positive factors, to wit, environmental stressing agents, virus and bacteria. Each of these factors separately produces adverse results on cattle, however, their combination is seen to exhibit additive effects. Environmental stresses vary in severity and effect, and the adverse conditions during transit from pasture or range to feedlot have been found to initiate the disease process. Weaning, vehicular vibrations, crowding, cooling and overheating also are noted as being among the physical factors, while fear, anxiety, and noise are deemed psychological factors. A more detailed discourse concerning the pathogenesis of shipping fever complex will be found in the following publication:

I. Diseases of Feedlot Cattle, by Jensen et al, Lea & Febiger, 2nd Ed. Philadelphia, Pa. 1971.

Investigations to the present have indicated that BRD (Shipping Fever Complex) is an interaction of several etiologic agents, *Pasteurella hemolytica* or *Pasteurella multocida*, Mycoplasma sp. and respiratory viruses, for instance, Myxovirus, parainfluenza-3(SF-4). These agents have been isolated singly and in combination from beef calves during outbreaks of BRD.

At the outset of the investigations, bacteriological and pathological studies resulted in the consistent isolation of *P. hemolytica* and/or *P. multocida* from diseased lungs. See for example the following publication:

II. Carter, G. R.: Observations on the Pathology and Bacteriology of Shipping Fever in Canada. Canad. J. Comp. Med., 18 (1954): 359–363.

When freshly isolated cultures of *P. hemolytica* and *P. multocida* were innoculated into healthy cattle, only variable results have been obtained, when the organisms in aerosol were administered into the nose, a mild febril reaction has been produced and essentially no reaction has been observed when similar orgnisims are injected subcutaneously. In this regard, see the following publications:

III. Baldwin, et al, Experimental Infection of Calves with Myxovirus Parainfluenza 3 and *Pasteurella Hemolytica*. AJVR 28 (1967): pp. 1773–1782

IV. Gale et al, Studies on Shipping Fever of Cattle. I. Experimental Exposure of Cattle with Various Cultures of Pasteurella. AJVR. 19 (1958): pp. 815–817.

Investigations seeking an immunoresponse to BRD through the use of Pasteurella bacterins have shown that, while high levels of serum antibody may be evoked, the animals tested generally were not protected against infection. It has been reported that mice vaccinated by the subcutaneous route were fully protected against parenteral challenge but only partially protected against aerogenic infection by *P. multocida*. See, for example:

V. Collins, F. M. and J. B. Woolcock. Immune responses to *Pasteurella multocida* in mouse. J. Reticuloendothelial Soc. 19, (1976), 5: 311–321.

Further, it has been shown that a single injection of *P. hemolytica* bacterin with Freund's adjuvant is, in fact, immunosuppressive to the antigens of sheep red blood cells. See:

VI. Wilkie, B. N., et al, Nonspecific immunosuppression induced in mice with killed *Pasteurella hemolytica* in Freund's Complete Adjuvant. Int. Archs. Allergy Appl. Immun. 50 (1976): 745–750.

The historical development of the research into bacterial pathogens as the cause of BRD led investigators to postulate that the primary cause was a viral agent. The initial isolation of such a virus occured in 1959 leading to the classification of the above identified myxovirus parainfluenza-3 (SF-4). See in this regard:

VII. Reisinger, et al, A Myxovirus (SF-4) Associated with Shipping Fever of Cattle, JAVMA. 135 (1959): 147–152.

When innoculated intranasally as an aerosol into healthy young cattle, the newly isolated virus usually caused a febrile reaction for about six days, but did not cause the entire antipical syndrome of BRD. (See publication VII above). However, the exposure of healthy cattle in close sequence to both myxovirus parainfluenza-3 (SF-4) and *P. hemolytica* or *P. multocida* caused more severe disease than virus alone, however the entire syndrome of Shipping Fever Complex has been described as not being reproduced, it being opined that the inclusion of a third positive factor, the above-noted appropriate environmental stress, may have been the requirement for full manifestation of the disease. See:

VIII. Heddleston, et al, Studies on the Transmission and Etiology of Bovine Shipping Fever, AJVR, 23 (1969) pp 548–553.

Following the noted isolation of viral agents, studies of the efficacy of an appropriate vaccine have been somewhat concentrated along the conventional techniques of using a modified live virus to stimulate the in vivo production of antibodies. The results of these efforts, however, have not been definitive (See publication I supra.). Some vaccines have been developed containing variable combinations of antigens from viral agents and bacterins, for instance, as described in U.S. Pat. No. 3,634,587. However, their efficacy is described as requiring further clarification (Publication I supra). At the present time all known immunizing agents appear to contain different combinations of attenuated live virus, inactivated virus and killed pasteurella sp., the latter being commonly referred to as "bacterins". Intranasal administration has been described as stimulating the formation of nasal secretion antibodies and may be more effective than parenteral innoculation (Publication I, supra).

The treatment of the disease once developed generally involves the administration of antibiotics as well as electrolytes and arsenical compounds in drinking water. However, at the present time, many feeder calf operations are experiencing an increased mortality in newly shipped cattle due to the emergence of strains of Pasteurella bacteria that are resistant to all antibiotics and chemotherapeutic drugs which are presently approved for a treatment of food-producing animals. These resistant strains have been isolated from several midwestern states and California. When outbreaks of BRD-SFC occured in groups of calves in which the resistant strains were present, morbidity has been as great as 90% and mortality has ranged from 10–20%. The widespread evolution of these drug-resistant strains of Pasteurella sp. indicates an important need for the development of an effective and practical vaccination procedure.

SUMMARY

The present invention is addressed to an improved vaccine and technique for immunizing livestock against respiratory disease of a type evidencing the presence of Pasteurella sp. bacteria, as well as to a method for providing the improved vaccine. Having a preferred application in the immunization of feeder calves against bovine respiratory disease induced from a stressing factor (shipping fever complex) the immunization method is characterized in the utilization of a live culture of a Pasteurella bacteria. This culture is administered by intradermal injection to evoke an immunoresponse found to be quite effective in the avoidance of Shipping Fever Complex, (SFC).

Another feature and object of the invention resides in the provision of a method for immunizing cattle against Bovine Respiratory Disease wherein a live culture of *Pasteurella hemolytica* is administered to calves by intradermal injection at a point in time within their lifespan prior to the subjection to a stressing factor. This point in time will be selected, for example, as being before weaning as well a before shipment to feedlots and the like. In the latter regard, an appropriate immunization time generally will be about two weeks before weaning. The situs of intradermal injection preferably is at the neck region.

It is a further object of the invention to provide a means of immunizing cattle against Bovine Respiratory Disease which can be carried out at practical low costs and reasonable convenience to the user.

In the latter regard, an advantage of the immunization procedure of the invention resides in its capability for effective coordination within present day cow-calf management systems, inasmuch as the technique does not entail a weaning procedure prior to sale. Generally, cow-calf producers would be unable or unwilling to accept the latter weaning procedure.

Another object of the invention is to provide an arrangement for significantly reducing the incidence of Bovine Respiratory Disease occasioned, inter alia, in consequence of shipment to a commercial feedlot and other stressing factors, as well as to increase the animals feed consumption, general health and well being during the feeding period by a practical vaccination procedure.

A further object of the invention is to provide an improved vaccine for animals serving to stimulate an antibody response with respect to respiratory disease of the type exhibiting Pasteurella sp. The vaccine is comprised of an infusion broth formed as an aqueous dispersion of proteinaceous material with antibody-free animal serum and supporting a live culture of *Pasteurella hemolytica* incubated therewithin over an interval selected to develop a bacteria population effective to stimulate an immune response in animals when administered thereto intradermally.

Another object of the invention is to provide a method of preparing a vaccine for animals serving to stimulate an antibody response with respect to respiratory diseases of the type exhibiting Pasteurella sp. which includes the steps of providing a seed culture of the bacteria, *Pasteurella hemolytica;* providing an infusion broth environment into which is admixed a quantity of antibody-free animal serum; adding select bacterial components of the seed culture to the infusion broth and incubating the bacterial components within the broth under agitation for an interval suited for deriving the noted vaccine. Preferably, the infusion broth is a brain-heart broth into which the fetal calf serum is added. Incubation preferably is carried out over an interval between about 18–24 hours and at a temperature of about 37° C.

Other objects of the invention will, in part, be obvious and will, in part, appear hereinafter.

The invention accordingly comprises the composition and methods possessing the components, steps and technique exemplified by the following detailed disclosure.

For a fuller understanding of the nature and objects of the invention, reference should be had to the following detailed description.

DETAILED DESCRIPTION

As indicated earlier herein, Bovine Respiratory Disease (BRD) induced in conjunction with stress factors (Shipping Fever Complex) is an interaction of several etiological agents, *P. hemolytica* or *P. multocida,* Mycoplasma sp. and respiratory viruses. Of these agents *P. hemolytica* particularly has emerged or evolved to strains which are resistant to all antibiotics and chemotherapeutic drugs that are presently approved for the treatment of food producing animals. *P. hemolytica* is described as a non-motile, non-spore forming encapsulated, coccoid, but pleomorphic rod which measures 0.25 to 0.4 by 0.6 to 2.6$\mu$ in size. In staining, it is gram-negative and bi-polar. On serum agar it forms round, smooth, moist colonies. The colonies of encapsulated organisms are iridescent. *P. hemolytica* is commonly found in the pneumonic lungs of cattle affected with the Shipping Fever Complex form of BRD and, additionally, is found in conjunction with lamb pneumonia as the latter is encountered somewhere between three weeks and two months of age. Additionally as noted above, Shipping Fever Complex forms of BRD are developed in conjunction with a stressing factor, that factor in feed calves being associated with transportation of the calves to feedlots as well as in weaning.

Looking to the stress induced through weaning, it may be observed that calves generally are raised from birth on pasture and travel at the side of their dams until about six months of age. During this growth period in most cases they are sustained by milk and grass. At weaning, however, the calves are abruptly moved from the milk supply and taken off grass and pasture. Further, the calves are separated from the dams and penned together. Generally, some period of time ensues before the calves adjust to the altogether different feed provided at the pens as well as accommodate to the altered environment. Transportation associated stress factors are readily apparent involving vibration and extreme environmental change.

In accordance with the invention, effective immunization against Shipping Fever Complex is achieved by immunizing calves with a vaccine containing a live culture of Pasteurella bacteria, the vaccinations being carried out by intradermal injection. Preferably, the live culture utilized is *Pasteurella hemolytica*. Additionally, it has been found important to carry out the vaccination prior to the occurence of a noted stressing period. In this regard, effective immunization has been realized where innoculation is carried out about two weeks prior to calf weaning.

Table I below provides data revealing that the instant vaccination procedure is not effective in the prevention of BRD (Shipping Fever Complex) if administered following a stressing period, for example transportation to a feedlot. The tabulation was generated from a study wherein 156 calves were obtained from six graded feeder calf sales in Ohio during a two week period. The calves received one of three protein supplements; (a) soybean meal, (b) urea or (c) soybean meal and urea. Aureo S-700 a product of American Cyanamid Corp., White Plains, N.Y. was added to the ration of one half of the above group. The calves were subdivided to receive: (a) intradermal vaccination with a live culture of *P. hemolytica*, (b) intradermal vaccination with a live culture of *P. hemolytica* and a subcutaneous injection of 1.5 mg./kg. of levamisole and (c) subcutaneous injection of 1.6 mg./kg. of levamisole. Additionally, an untreated control group was designated.

Ninety-one of the steers identified in Table I as "Group 1" received the vaccination treatment at an interval of two weeks in advance of the remaining sixty-five steers identified as "Group 2". Nasal specimens were taken at weekly intervals and cultured on blood agar plates. The overall incidence of BRD (Shipping Fever Complex) among the 156 was 88.4% and the total mortality rate was 10.25%. This outbreak of Shipping Fever Complex commenced five days after the arrival of the "Group 2" calves and continued for the ensuing four weeks. The vaccinated steers had a disease incidence of 73%, while the unvaccinated control steers had an 87% disease incidence. The major etiologic agents in the outbreak of Shipping Fever Complex were antibiotic resistant strains of *P. hemolytica*. Fifty-three percent of the isolates of *P. hemolytica* were sensitive only to erythromycin. Only 37.6% of the isolates were sensitive to the antibiotics usually used to treat cases of Shipping Fever Complex. These strains sensitive to tetracycline and/or erythromycin were only sensitive in a marginal sense. Additionally, antibiotic-resistant strains of *P. hemolytica* were isolated from the lungs of all of the steers that died during this outbreak.

The incidence of disease was not influenced by the injection of levamisole, and the relatively high incidence of antibiotic resistant strains of *P. hemolytica* was found to complicate the treatment of clinical cases of shipping fever. In the latter regard, the average rate of repeat treatment among the Group 2 calves was five per animal compared to 1.8 and 2.9 per animal for the vaccinated and control lots of Group 1, respectively. Treatment with penicillin was ineffective and treatment with high levels of tetracycline and erythromycin only tended to control the course of the disease.

Preparation of the live culture utilized in the vaccination procedures of the invention, including the trials thereof described later herein, involves the initial isolation of *Pasteurella hemolytica* from a field case of BRD-Shipping Fever Complex: (SFC). For maintenance purposes, a calf is infected by an intravenous injection of the culture. As the calf becomes moribund, it is euthanitized, or following its death due to BRD-SFC, the liver thereof is removed. Small portions of the liver are placed in plastic test tubes and maintained in a continuous frozen state at $-70°$ C.

A seed culture is obtained by streaking a defrosted portion of the retained liver on blood agar plates accompanied by incubation for eighteen hours at 37° C. At the termination of that eighteen hour period, a typical *P. hemolytica* is selected and seeded into brain-heart infusion broth, following which it is incubated for eighteen to twenty-four hours at 37° C. with continuous agitation. The latter agitation may be provided by a conventional laboratory shaker device. Two percent, by volume, fetal calf serum is added to the infusion broth to provide a protein enhancement of culture growth. Fetal calf serum is utilized for this growth enhancement to assure avoidance of the introduction of antibodies into the broth. The resultant vaccine is administered in an effective dosage, for instance about 1 cc. The broth utilized in the trials described herein is identified as Bacto Brain Heart Infusion Broth, a product of DIFCO Laboratories, Detroit, Mich.

TABLE I

The Incidence of Shipping Fever Complex Mortality and Frequency of Treatment in Vaccinated and Nonvaccinated Steers.

| Group | No. | Cases SFC | % SFC | No. of Treatments | Treatment Rate | Mortality |
|---|---|---|---|---|---|---|
| 1 Vaccinated | 48 | 35 | 73 | 87 | 1.8 | 0 |
| Not Vaccinated | 43 | 39 | 87 | | 2.9 | 2 |
| Sub Total | 91 | 74 | 81.3 | 213 | 2.3 | |
| 2 Vaccinated | 36 | 35 | 97 | 183 | 5.0 | 9 |
| Not Vaccinated | 29 | 29 | 100 | 126 | 5.6 | 5 |
| Sub Total | 65 | 64 | 98 | 346 | 5.3 | |
| Total | 156 | 138 | 88.4 | 559 | 3.6 | 16(10.25%) |

Turning now to trials carried out in connection with the varification of the instant vaccination technique, reference initially is made to Table II below. The calves represented in the table were reared in four widely separated pasture lots located at the Eastern Ohio Resource and Development Center in southeastern Ohio. This center is identified as "EORDC" in the table. Two weeks prior to a scheduled weaning date, 79 calves were designated controls and the remaining calves were subdivided to receive a specified vaccine treatment. In the latter regard, fifteen of the calves were administered a conventional combined modified live viral vaccine, IBR-PI-3 (Infectious Bovine Rhinotracheitis)-(Parainfluenza-3). This combined viral vaccine was administered intranasally using a 2 ml. dosage per calf.

Forty-two of the calves were administered the above modifed combined live viral vaccine utilizing intranasal technique, in addition to an intradermal administration, at the neck situs, of a live culture of *Pasteurella hemolytica*, in 1 cc dosage per calf. Twenty-seven of the calves were administered a 1 cc dosage of a live culture of *Pasteurella hemolytica*. The latter administration was provided by intradermal injection at the neck situs.

Following immunization treatment as above, the calves were returned to pasture with their dams. At the time of weaning, 79 of the calves were trucked directly, 81 miles, to the Ohio Agricultural Research and Development Center (OARDC) at Wooster, Ohio, as identified in the upper portion of Table II.

TABLE II

The incidence of bovine respiratory disease* among calves receiving intradermal and intranasal vaccination.

| No. of calves | Vaccine treatment | Cases BRD* | % BRD* |
|---|---|---|---|
| EORDC direct to Wooster, Ohio | | | |
| 25 | Control (nonvaccinated) | 0 | 0 |
| 13 | IBR-PI-3 (intranasal) | 1 | 9.6 |
| 23 | IBR-PI-3 (intranasal) plus *P. hemolytica* (intradermal) | 1 | 4.3 |
| 18 | *P. hemolytica* (intradermal) | 0 | 0 |
| | | 2 | 2.5 |
| EORDC to an auction barn and then to the Mahoning County farm | | | |
| 54 | Control (nonvaccinated) | 9 | 16.3 |
| 2 | IBR-PI-3 (intranasal) | 0 | 0 |
| 19 | IBR-PI-3 (intranasal) plus *P. hemolytica* (intradermal) | 0 | 0 |
| 9 | *P. hemolytica* (intradermal) | 0 | 0 |
| | | 9 | 10.5 |

*Shipping Fever Complex

Essentially simultaneously, 84 of the calves were moved to, and held, at an auction barn for 48 hours and then trucked by commercial carrier 121 miles to a farm operated by Mahoning County, Ohio, located at Canfield, Ohio. Upon arrival at each of the noted sites, all animals were comingled within adjacent pens. The incidence of BRD-Shipping Fever complex in these groups of calves is presented in Table II. Table II reveals that although the incidence of respiratory diesase is not extensive in these groups, the results indicate that the intradermal vaccination with a live culture of *Pasteurella hemolytica* is effective in the prevention of BRD-Shipping Fever Complex and that this vaccine can be used safely in conjunction with intranasal virus vaccines.

Referring to Table III below, the results of a second trial utilizing the vaccination procedure of the invention are tabulated. In this trial, calves (principals) were vaccinated intradermally at the neck situs with a culture of live *P. hemolytica*. Vaccination with single, 1 cc dosages occured two weeks prior to wearing at the noted Mahoning County Ohio farm. At the time of weaning, the vaccinated calves were trucked to and penned at an auction barn for forty-eight hours for natural exposure to the infecting agent of BRD (Shipping Fever Complex). Following this forty-eight hour interval, the calves were trucked to the Beef Research Unit, Ohio Agricultural Research and Development Center (OARDC), Wooster, Ohio. The control calves were auction purchased calves obtained at the same sale as well as at several other sales over a subsequent two week period. All animals were comingled in several adjacent pens in approximately equal numbers. The incidence of BRD (Shipping Fever Complex), sickness interval, mortality and numbers of culls are set forth in Table III. The "cull" designation represents a calf judged to be unfit for further treating. The table reveals that those calves which received an intradermal vaccination with live *Pasteurella hemolytica* culture had a significantly lower incidence of BRD (Shipping Fever Complex) and there were no deaths or cull losses in this group as compared to a 43% morbidity, a 14.9% mortality, and an 11.1% cull rate among the group.

Among the animals represented in Table III, 44% of 117 isolants of *Pasteurella hemolytica* were resistant to penicillin, tetracycline, erythromycin, streptomycin and sulfonamides and 48% of the isolants were resistant to tetracycline, erythromycin, streptomycin and sulfonamides. A mere eight percent of the isolants were sensitive to chemoprophylactic drugs approved for use in food-producing animals.

No severe untoward reactions were observed as a result of the vaccination procedure utilized in the trials. A swelling may be observed to arise at the injection site within one hour following the injection and the swelling may persist for a period of six to twelve hours. A small area of induration may be pulpated for a period of a few days and usually, this is not apparent at seven days. The indurated tissue regresses without treatment during a thirty-day period.

TABLE III

The incidence of bovine respiratory disease* and mortality among weaned and shipped calves receiving an intradermal vaccination

| No. of calves | Vac. treat. | Cases BRD* | % BRD | Total days sick | Ave. days sick | Mort. | % Mort. | Culls** | % Culls |
|---|---|---|---|---|---|---|---|---|---|
| 54 | Control | 25 | 46.3 | 47 | 1.8 | 8 | 14.9 | 6 | 11.1 |
| 24 | *P. hemolytica* (Intradermal) | 1 | 4.1 | 1 | 1 | 0 | 0 | 0 | 0 |

*Shipping Fever Complex
**Culls judged to be unfit for further feeding

As indicated above, the intradermal route of vaccination with bacterial antigens according to the invention has been found to be an important aspect in developing protective immunity. This intradermal route has not been the subject of attention on the part of investigators over the recent past. Early basic research nonspecific to immunology has been carried out in connection with rabbits. For example, studies of intradermal vaccination of rabbits with heat-killed and live cultures of pneumococci have been reported, in the following publications:

IX. Goodner, K. Experimental intradermal pneumococcus infection in rabbits, J. Exp. Med. 48, (1928):1-20.

X. Julianelle, L. A. Reactions of rabbits to intracutaneous injections of pneumococci and their products. I. The antibody response. J. Exp. Med. 51, (1930); 441-448.

XI. Julianelle, L. A. Reactions of rabbits to intracutaneous injections of pneumococci and their products. II. Resistance to infection. J. Exp. Med. 51, (1930): 449-462.

XII. Julianelle, L. A. Reactions of rabbits to the intracutaneous injection of pneumococci and their products. III. Reactions at the site of infection. J. Exp. Med. 51 (1930): 463-472.

It was observed in the course of these somewhat dated studies that immune response of rabbits vaccinated intradermally was different than the response of those receiving subcutaneous or intravenous vaccination. Publication IX above describes that intradermal innoculation of rabbits with live organisms effected the development of an immune system without the appearance of agglutinating or precipitating antibodies. Publications X-XII above describe the utilization of repeated vaccination with killed organisms to demonstrate a protection to an intravenous challenge with pneumococci in the absence of type specific agglutinins.

Efforts at immunization carried out using Pasteurella bacterins (killed bacteria) often have been evaluated on the basis of evoked serum antibodies in accordance with conventional practice. While high levels of such serum antibodies may be developed, it has been observed that the innoculated animals may not be protected against infection. For example, it has been reported that mice vaccinated by the subcutaneous route were fully protected against parenteral challenge, but only partially protected against aerogenic infection by *P. multocida*. See publication V above in this regard. Additionally as noted in conjunction with Publication IV above, it has been shown that a single injection of *P. hemolytica* bacterins with Freund's adjuvant is immunosuppressive to the antigens of sheep red blood cells. The lack of definition of the precise immunoresponse mechanism is further borne out in connection with investigations deriving the first effective vaccine for turkeys. In this regard, reference is made to the following publications:

XIII. Bierer, B. W. et al. Immunologic response of turkeys to an avirulent *Pasterurella multocida* vaccine in drinking water. Poul. Sci. 51 (1972), 2: 408-416.

XIV. Bierer, B. W. et al. Immunologic response of turkeys to an avirulent *Pasteurella multocida* vaccine in drinking water. Poul. Sci. 51, (1972), 4: 1402-1408.

XV. Bierer, B. W. et al. Immunological response to turkey poults of various ages to an avirulent *Pasterurella multocida* vaccine in drinking water. Poul. Sci. 1, 54, (1975), 3:784-787.

The above publications report upon studies of the immunologic response of turkeys to an avirulent *P. multocida* in drinking water and have found the technique represented thereby to be effective in the prevention of Pasteurella infections. More particularly, it has been demonstrated that an oral immunization of turkeys and chickens results in a protective immune response that is not necessarily related to Precipitins or agglutinins, i.e. serum antibody responses. In the latter regard mention may be made of the following publication:

XVI. Heddleston, K. L., et al. Fowl Cholera-immunological and serologic response in turkeys to live *Pasteurella multocida* vaccine administered in the drinking water. Poul. Sci. 54, (1975), 1: 217-221.

As is apparent, the above developments concern a related bacterial strain and the utilization of a living organism. Of course, a different husbandry procedure is involved in the raising of turkeys, no weaning being required. However, the same natural infection route, the intestinal tract, is involved in the immunization mechanism.

Further with respect to the immunization response mechanism, cell-mediated immune responses of turkeys have been investigated and reported in the following publication:

XVII. Maheswaran, S. K. et al Studies on *Pasteurella multocida*. III. In vitro assay for cell-mediated immunity. Avian Dis. 20, (1976): 332-341.

The latter publication demonstrates that turkeys immunized orally with a live attenuated strain of *P. multocida* contained a population of peripheral lymphocytes which are stimulated by an in vitro culture with *P. multocida* antigens. The publication suggests the nature of immunity associated with *P. multocida* infections in turkeys is not known but that the investigation of lymphocyte transformation assay coupled with humoral immune response may further define the problem. Additionally, it has been demonstrated that the introduction of antigens in a manner so as to stimulate secretory and humoral antibody is important for complete protection of chickens. In this regard, reference can be made to the following publication:

XVIII. Wichmann, R. W. et al. The protective effect conferred by *Pasteurella multocida* bacterin administered intranasally, Avian Dis. 18, (1974):631-633.

In the latter investigation, the benefits of combining subcutaneous and intranasal immunization techniques using a Pasteurella bacterin were studied. The report concludes that a combination vaccination program is superior to the subcutaneous form of vaccination alone. Two doses of bacterin are required in the study, such vaccinations being administered at two week intervals along with a vaccination regimen which must be completed two weeks prior to challenge.

Further outlining the complexity of the immune response mechanism, several investigators have shown that the intranasal installation of inactivated or live virus results in the production of secretory antibody and little or no serum antibody titer. In this regard, reference may be made to the following publication:

XIX. Waldman, R. H. et al. Immunity to infections on secretory surfaces. J. Inf. Dis. 130 (1974):419-440.

The above publication reports that when intranasally vaccinated individuals were challenged with virulent virus, those with secretory antibodies were protected while those vaccinated via the intramuscular route were not protected.

The immune response in rabbits to killed *P. hemolytica* administered via aerosol and/or intramuscularly also has been the subject of investigation, reference being made to the following publication:

XX. Wilkie, B. N. et al. Effect of route of immunization on lapine immune response to killed *Pasteurella haemolytica* and influence of aerosol challenge. Canad. J. Comp. Med. 40 (1976), 4:346–349.

The above publication describes that repeated immunization of rabbits using either the aerosol or intramuscular route or combination of both was found effective in the production of antibody in serum and bronchoalveolar washings. The publication further shows that aerosol challenge with live cultures of *P. hemolytica* served as the greatest stimulation to an immune response, suggesting that live but attenuated, vaccines may be developed to control BRD. Similarly, Publication VI (supra) cites investigation wherein the immunization of calves with killed *P. hemolytica* by aerosol and subcutaneous injection in Freund's complete and incomplete adjuvant was found to be without protective effect on the development of pneumonia after challenge with live *P. hemolytica*. The citation is reported to have observed that there was an inverse correlation between *P. hemolytica* specific antibody titers in bovine nasal washing and the severity of pneumonia after challenge.

As the above works demonstrate, the immune response mechanism in diseases exhibiting Pasteurella sp., including BRD-Shipping Fever Complex remains conjectural to investigators. It is opined that the works demonstrate that the cellular, humoral and secretory immune systems can be stimulated by bacterial antigens and that each of these systems may be important to the defense of the host against infection. It further is opined that the intradermal vaccination with live cultures of *P. hemolytica* in accordance with the procedure of the invention tends to stimulate the cellular immune response.

In view of the above, it may be observed that the several objects of the invention are achieved and other advantageous results attained.

Inasmuch as various changes could be made in the above methods and vaccine composition without departing from the scope of the invention, it is intended that all matter contained in the above description should be interpreted as illustrative and not in a limiting sense.

What is claimed is:

1. A method of immunizing cattle against respiratory disease of the type exhibiting the presence of Pasteurella sp. comprising administering, by intradermal injection prior to a stressing period, an immunologically effective amount of a vaccine containing a live culture of a *Pasteurella hemolytica* bacteria.

2. The method of immunizing cattle as set forth in claim 1 wherein said intradermal injection is carried out upon calves about two weeks prior to the weaning thereof.

3. The method of immunizing cattle as set forth in claim 1 wherein said culture is incubated within a brain-heart infusion broth over an incubation period of about 18–24 hours.

4. The method of immunizing as set forth in claim 3 wherein said vaccine is administered to calves prior to the weaning thereof.

5. The method of immunizing as set forth in claim 4 in which said culture is injected in about a one cubic centimeter dosage amount.

6. An improved vaccine for stimulating antibody response in cattle to respiratory diseases of the type exhibiting the presence of Pasteurella sp. said antibody response being evoked by the intradermal injection thereof into said cattle prior to the occurence of a stressing period, said vaccine consisting essentially of:
   brain-heart infusion broth present as an aqueous dispersion of proteinaceous material;
   an antibody-free fetal calf serum admixed with said broth and initially present in said broth in an amount representing about 2% by volume; and
   a field strain live culture of *Pasteurella hemolytica* incubated within said serum containing broth over an interval selected to drive a bacterial population effective to stimulate an immune response within said cattle following the said intradermal injection thereof.

7. The improved vaccine of claim 6 wherein said incubation period is selected as about 18–24 hours.

8. The method of preparing a vaccine for cattle serving to stimulate an antibody response to respiratory disease of the type exhibiting the presence of Pasteurella sp. said antibody response being evoked by the intradermal injection thereof into said cattle prior to the occurence of a stressing period, said method comprising the steps of:
   providing a field strain seed culture of the bacteria, *Pasteurella hemolytica;*
   providing a brain heart infusion broth present as an aqueous dispersion of proteinaceous material into which is admixed about 2% by volume of antibody-free fetal calf serum;
   adding a select bacterial component of said seed culture to said infusion broth; and
   incubating said bacterial component within said broth under agitation for an interval suitable for deriving a *Pasteurella hemolytica* bacteria population effective to stimulate an immune response when said live bacteria containing broth is administered intradermally to a said animal.

9. The method of claim 8 wherein said step of incubating said bacterial component within said broth is carried out over an interval selected between about 18–24 hours and at a temperature of about 37° C.

10. The method of claim 8 in which said seed culture is provided by:
   providing a portion of the liver of a calf infected by a culture of Pasteurella sp.;
   applying a portion of said liver in a defrosted state to a blood agar plate;
   incubating said blood agar plate for an interval of time adequate to generate a culture of P. hemolytica thereupon; and
   selecting a typical P. hemolytica culture incubated upon said blood agar plate.

* * * * *